(12) United States Patent
Kuperus et al.

(10) Patent No.: US 9,901,233 B2
(45) Date of Patent: Feb. 27, 2018

(54) AIR FILTER MONITORING

(71) Applicant: KONINKLIJKE PHILIPS N.V., Eindhoven (NL)

(72) Inventors: Johan Bernard Kuperus, Eindhoven (NL); Johannes Tseard Van Der Kooi, Eindhoven (NL); Bastiaan Johannes De Wit, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 82 days.

(21) Appl. No.: 15/030,474

(22) PCT Filed: Nov. 5, 2014

(86) PCT No.: PCT/EP2014/073831
§ 371 (c)(1),
(2) Date: Apr. 19, 2016

(87) PCT Pub. No.: WO2015/078672
PCT Pub. Date: Jun. 4, 2015

(65) Prior Publication Data
US 2016/0256026 A1 Sep. 8, 2016

(30) Foreign Application Priority Data
Nov. 26, 2013 (EP) ..................................... 13194356

(51) Int. Cl.
A47L 9/19 (2006.01)
A47L 9/28 (2006.01)
G01N 15/08 (2006.01)

(52) U.S. Cl.
CPC ................ *A47L 9/19* (2013.01); *A47L 9/2842* (2013.01); *G01N 15/0826* (2013.01); *G01N 2015/084* (2013.01)

(58) Field of Classification Search
CPC . A47L 9/19; A47L 9/28; A47L 9/2842; G01N 15/00; G01N 15/08; G01N 15/0826; G01N 15/084
See application file for complete search history.

(56) References Cited

U.S. PATENT DOCUMENTS 2,532,642 A 12/1950 Senne
4,294,595 A 10/1981 Bowerman
(Continued)

FOREIGN PATENT DOCUMENTS

EP 0479609 A2 4/1992
GB 712270 A 7/1954
(Continued)

*Primary Examiner* — Nguyen Ha

(57) ABSTRACT

In a method of monitoring pollution of an air filter (Filt1) in a device in which an air flow (A) generated by a fan (F) engaged by a motor (M) passes the air filter (Filt1), the pollution is determined using data representative of a pressure difference (D2) over the fan (F), a pressure difference (D1) over the air filter, and a motor current (I) to the motor (M). The method comprises the steps of: estimating a flow through the air filter from data representative of the pressure difference (D2) over the fan (F), and the motor current (I) to the motor (M), estimating a filter resistance of the air filter from data representative of the flow through the air filter, and the pressure difference (D1) over the air filter, and estimating the pollution of the air filter from data representative of the filter resistance of the air filter.

4 Claims, 1 Drawing Sheet

(56) References Cited

U.S. PATENT DOCUMENTS

| | | | |
|---|---|---|---|
| 4,983,895 A | | 1/1991 | Koharagi |
| 5,243,732 A | * | 9/1993 | Koharagi .............. A47L 9/2821 15/319 |
| 5,294,872 A | | 3/1994 | Koharagi |
| 7,261,762 B2 | | 8/2007 | Kang |
| 2007/0277592 A1 | * | 12/2007 | Johansson .......... B01D 46/0086 73/38 |
| 2008/0229719 A1 | * | 9/2008 | Hayama .................... A47L 7/02 55/283 |
| 2008/0244858 A1 | | 10/2008 | Shaver |
| 2011/0271480 A1 | | 11/2011 | Kara |

FOREIGN PATENT DOCUMENTS

| | | | | |
|---|---|---|---|---|
| JP | 2008301878 A | | 12/2008 | |
| WO | 9797728 A1 | | 3/1997 | |
| WO | WO 2015078672 A1 | * | 6/2015 | ............... A47L 9/19 |

\* cited by examiner

AIR FILTER MONITORING

This application is the U.S. National Phase application under 35 U.S.C. § 371 of International Application No. PCT/EP2014/073831, filed on Nov. 5, 2014, which claims the benefit of International Application No. 13194356.5 filed on Nov. 26, 2013. These applications are hereby incorporated by reference herein.

FIELD OF THE INVENTION

The invention relates to a device (e.g. a vacuum cleaner or an air cleaner) comprising an air filter, and to a method of air filter monitoring.

BACKGROUND OF THE INVENTION

Vacuum cleaners have the disadvantage that filters will get clogged after some time of use. This phenomenon is hard to perceive by users, because the pollution of the filters is a slow process. In normal use it can take more than half a year before the performance of the vacuum cleaner is impaired.

Some vacuum cleaners are equipped with a pressure switch, measuring the pressure difference over a filter. The disadvantage of this principle is that, at varying flow, the pressure difference does not relate directly to the filter pollution. When lowering the flow by changing the setting of the speed regulator, the pressure difference will decrease and thus the signal generated by the pressure switch might change from 'polluted' to 'clean', whereas the filter pollution has not changed. There will also be a substantial difference in flow if the vacuum cleaner is used on carpet compared to the use on hard floors.

JP2008301878 provides a vacuum cleaner capable of detecting the clogging of a filter through which air from a dust collection chamber passes toward an electric fan. The dust sucked by the operation of the electric fan is stored inside a dust cup, and air from the dust cup passes through the filter toward the electric fan. The amount of the dust stored in the dust cup is detected by a dust sensor, and the air flow rate of the electric fan is detected by an air flow rate detection part based on the change of the electric current in the electric fan. When the result of detection by the dust sensor suggests that the amount of the dust is not more than a prescribed quantity and when the result of detection by the air flow rate detection part suggests that the air flow rate is not more than a prescribed small air flow rate, a filter clogging determining part determines that the filter is clogged.

U.S. Pat. No. 4,294,595 discloses an automatic shutoff arrangement for a vacuum cleaner of the "clean air" type in which the vacuum fan is downstream of the dirty air passageway and vacuum filter. A pressure differential or air flow responsive switch is connected between the nozzle inlet to the dirty air passageway of the vacuum and the clean air passageway after such air flow has passed through the filter bag. The pressure differential switch is operable in response to a change in the flow of air through the system and causes power to the vacuum motor to be interrupted and simultaneously gives a warning to the operator that the filter is full or that a blockage exists somewhere along substantially the entire length of the dirty air passageway.

U.S. Pat. No. 5,294,872 discloses a vacuum cleaner in which by detecting a rotational speed of a variable speed fan motor adapted to give a suction force to the cleaner and its change range, the choking state of the filter and the state of the cleaned surface are discriminated, and a speed command of the fan motor is corrected on the basis of the result of the discrimination, and comfortable cleaning can be performed by the optimum suction force.

Prior art filter monitoring systems do not effectively cope with flow variation and the power setting. This will lead to systems that signal a polluted filter correctly and after lowering the power will show a non-polluted filter again, whereas the filter is still as polluted as it was. On the other hand these appliances will show a polluted filter too early at high flows, e.g. when the nozzle is not on the floor.

SUMMARY OF THE INVENTION

It is, inter alia, an object of the invention to provide an improved air filter monitoring. The invention is defined by the independent claims. Advantageous embodiments are defined in the dependent claims.

In a method of monitoring pollution of an air filter in a device in which an air flow generated by a fan engaged by a motor passes the air filter, the pollution is determined using data representative of a pressure difference over the fan, a pressure difference over the air filter, and a motor current to the motor.

A combination of measuring a pressure difference over the fan, and the motor current has shown to deliver a reliable flow prediction irrespective of the power setting.

The combination of the flow prediction and the pressure drop over the filter can be combined to a parameter related to the filter resistance, and thus the pollution.

The air filter may be the motor filter, the exhaust filter, or any other filter in the flow path.

These and other aspects of the invention will be apparent from and elucidated with reference to the embodiments described hereinafter.

DESCRIPTION OF EMBODIMENTS

Figure 1:
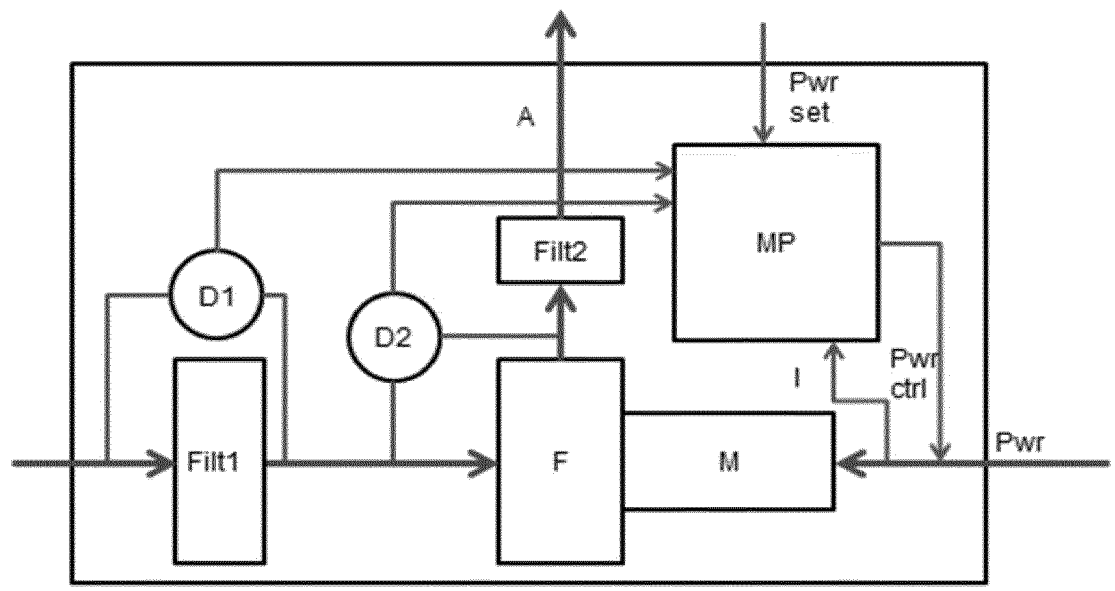
FIG. 1 shows an embodiment of a device in accordance with the present invention.

FIG. 1 shows an embodiment of a device in accordance with the present invention. An air flow A passes a motor filter Filt1, a fan F that is engaged by a motor M receiving an electrical power signal Pwr, and an exhaust filter Filt2. A first pressure difference sensor D1 measures a pressure difference over the motor filter Filt1, and a second pressure difference sensor D2 measures a pressure difference over the fan F. A microprocessor MP receives signals from the pressure difference sensors D1 and D2, as well as a power setting signal Pwr set, the current I through the motor M, so as to produce a power control signal Pwr ctrl for the motor M.

The invention is based on the following considerations. The filter resistance will increase when the filter gets polluted. The filter resistance can be known by knowing the air flow and the pressure difference over the motor filter Filt1. Measuring only the pressure difference over the filter Filt1 as an indication of the filter pollution is a known solution. However, as the power setting Pwr set of the appliance can be regulated by the end user, the flow will vary and thus the pressure difference over the filter Filt1. Thus under these varying circumstances one has to know both the air flow and the pressure difference to establish the resistance of the filter. Direct measurement of the flow is relatively expensive and complicated. Deriving the flow out of a combination of in- and outgoing parameters of the motor-fan combination has been investigated. A combination of measuring the pressure rise Δp over the fan F and the motor current I has shown to deliver a reliable flow prediction irrespective of the power setting Pwr set. Measuring the motor voltage is less attractive, because the motor is relatively temperature sensitive at constant voltage. Measuring the motor speed would be an option, but is more expensive than measuring the motor current.

In a device having an air filter, the following parameters are available.
U=Mains voltage
I=Motor current
Ũ=Voltage to motor as provided by a speed regulator
ω=Rotational speed of motor and fan
T=Torque of motor and fan
Φ=Air flow produced by fan
Δp=pressure built by fan Whereas measuring the air flow is rather complicated in household vacuum cleaners, part of the invention is to derive an approximation of the flow from other parameters out of the list above by means of calculation. A preferred method is the calculation of flow as a function of Δp and I. Another method is the calculation of flow as a function of Δp and ω, or (although more complex) to use T instead of I; ω or T could thus be used as data representative of I within the meaning of the claims. The measurements, including the filter pressure difference, are fed into a microprocessor that will do the calculation by means of the determined algorithm and will generate a parameter related to the level of filter pollution. Depending on the value of this parameter, information will be generated that can be used to give feed back to the user about the filter status. This information could also be used to control functions in the vacuum cleaner, for instance to control flow.

A mathematical approach is as follows. If a motor filter in a vacuum cleaner gets polluted over time, its resistance will rise. The resistance of a filter can be described, by common fluid dynamics, as:

$$R_{Filt} = \Delta p_{Filt} / \Phi_{Filt}^2 \qquad [1]$$

Wherein:
$R_{Filt}$=Filter resistance
$\Phi_{Filt}$=Air flow through filter
$\Delta p_{Filt}$=Pressure difference over filter This means that the resistance can be calculated, knowing the flow and the pressure difference. The pressure difference $\Delta p_{Filt}$ can be measured by means of a pressure sensor.

The flow $\Phi_{Filt}$ could be measured, but this is relatively complicated. Therefor the idea is to calculate the flow out of known, or simply measurable, system parameters.

Experiments have shown that a combination of motor current and pressure build up by the motor can deliver a mathematical model describing the flow with sufficient accuracy.

In general this relation can be written as:

$$\Phi_{Filt} = \Phi_{Motor} = f(I_{Motor}, \Delta p_{Motor}) \qquad [2]$$

wherein:
$I_{Motor}$=Motor current
$\Delta p_{Motor}$=pressure built up by motor
This function $f$ describes a surface in the ($\Phi_{Filt}$, $I_{Motor}$, $\Delta p_{Motor}$) space.

Via measurements one can find multiple points on this surface. By means of processing the measured data with multiple nonlinear regression one can find an approximation of this surface in the form of a three dimensional polynomial function.

Calculation Process:
Measured Values $$\begin{bmatrix} I_1 & \Delta p_1 & \Phi_1 \\ I_2 & \Delta p_2 & \Phi_2 \\ I_3 & \Delta p_3 & \Phi_3 \\ \ldots & \ldots & \ldots \\ \ldots & \ldots & \ldots \\ \ldots & \ldots & \ldots \\ I_{q-1} & \Delta p_{q-1} & \Phi_{q-1} \\ I_q & \Delta p_q & \Phi_q \end{bmatrix}$$

Wherein:
q=is number of measurements
Via multiple nonlinear regressions these can be converted to a polynomial approximation:

$$\Phi_{approximated} = \Sigma_{m=0}^{m=N} \Sigma_{n=0}^{n=N} a_{nm} \cdot I^n \cdot \Delta p^m, m+n \leq N \qquad [3]$$

Wherein:
N=degree of polynomal
$a_{mn}$=polynomal coefficient

In general the approximation will be more accurate at higher degrees. In practice the degree (N) is chosen in such a way, that the accuracy is within the requirements.

Example of the approximation:
Measurements have shown that a second degree approximation, with N=2, seems to suffice to estimate the flow within 5% accuracy.

In case N=2, the polynomial is written as:

$$\Phi_{approximated} = a_{00} + a_{10} \cdot I + a_{20} \cdot I^2 + a_{11} \cdot I \cdot \Delta p + a_{01} \cdot \Delta p + a_{02} \cdot \Delta p^2 \qquad [4]$$

The coefficients $a_{m,n}$ can be determined via the method as described and be put as fixed numbers into the microprocessor. By putting the formula as algorithm into the microprocessor as well, the flow can be calculated with the measured current and pressure built up as inputs.

To be able to put the coefficients as fixed values into the microprocessor, one should be sure that the accuracy for individual vacuum cleaners is still fulfills the requirements. To achieve this, an algorithm is calculated based upon measurements of multiple appliances and this 'average' algorithm is compared with the individual measurements.

It may be clear that the coefficients are depending on the actual execution of the vacuum cleaner. Motor and fan characteristics will show some variation, but within one product design this variation is expected to be low enough to meet the accuracy specifications. In practice this will mean that all different product designs will have the same algorithm, but only the coefficients will be different. These coefficients can be loaded into the microprocessor after loading the algorithm. Via formula [1] and the measurement of the pressure difference over the filter, the resistance of the filter can be calculated. As soon as the resistance surpasses a predefined value, the signal for a polluted filter is generated.

In a test environment, good results were obtained by using the following formula (with Φ in [l/s], Δp in [hPa], and I in [A]):

$$\Phi_{approximated} = -15.612 + 13.434 \cdot I - 0.29 \cdot \Delta p + 0.039 \cdot I \cdot \Delta p - 0.877 \cdot I^2 - 0.00013 \cdot \Delta p^2 \quad [5]$$

In an actual environment, suitable coefficients can be found by measuring the actual flow and tuning the coefficients until the approximated flow sufficiently measures the actual flow. These coefficients can then be programmed into the microprocessor MP.

Figure 2:
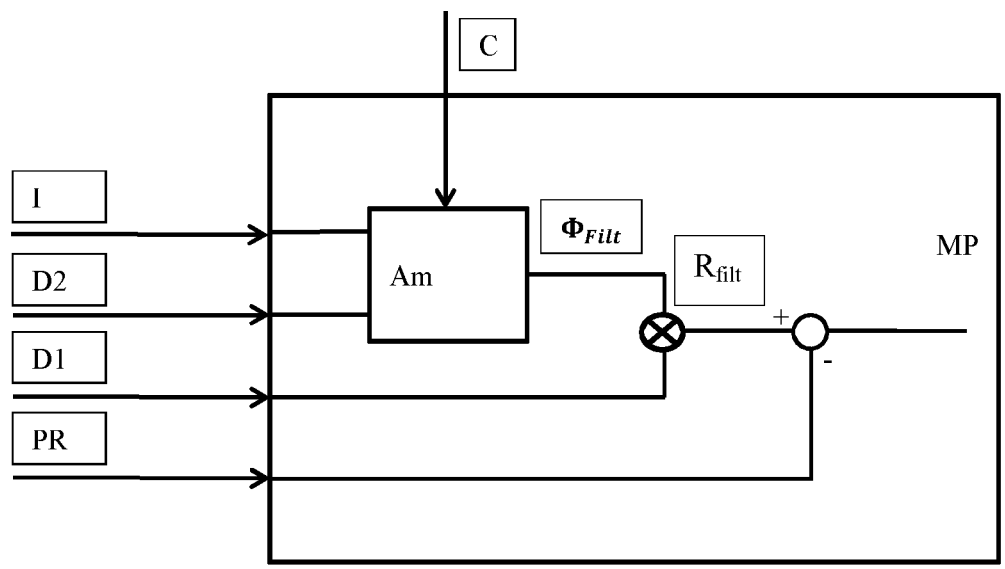
FIG. 2 illustrates an embodiment of the operation of a microprocessor in the device of FIG. 1.

In view of the above considerations, FIG. 2 illustrates the operation of the microprocessor MP in the device of FIG. 1. In the microprocessor MP, by means of an algorithm Am using coefficients C, the flow $\Phi_{Filt}$ is calculated from the motor current I and the pressure difference over the fan as determined by the second pressure difference sensor D2. The filter resistance $R_{filt}$ is calculated from the flow $\Phi_{Filt}$ and the pressure difference over the motor filter Filt1 as determined by the first pressure difference sensor D1. The filter resistance is representative of the pollution of the air filter: the higher the pollution, the higher the filter resistance will be.

If it is desired to have a binary output on whether the air filter needs to be replaced or cleaned (e.g. to switch on a warning light), a preset resistance PR can be subtracted from the filter resistance $R_{filt}$: if the difference is positive, the filter is too polluted and should be replaced or cleaned, while if the result is negative, the filter is not yet too polluted and does not yet need to be replaced or cleaned.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention may be implemented by means of hardware comprising several distinct elements, and/or by means of a suitably programmed processor.

The invention claimed is:

1. A method of monitoring pollution of an air filter (Filt1) in a device in which an air flow (A) generated by a fan (F) engaged by a motor (M) passes the air filter (Filt1), wherein the method comprises the steps of:

estimating a flow through the air filter from data representative of a pressure difference (D2) over the fan (F), and a motor current (I) to the motor (M), and estimating a filter resistance of the air filter from data representative of the flow through the air filter, and a pressure difference (D1) over the air filter, estimating pollution of the air filter from data representative of the filter resistance of the air filter.

2. A method as claimed in claim 1, wherein the pollution of the air filter is estimated from comparing the filter resistance of the air filter with a threshold value (PR).

3. A device comprising:

an air filter (Filt1), a motor (M) coupled to a fan (F) for generating an air flow through the air filter (Filt1), and a processor (MP) for determining pollution of the air filter (Filt1), wherein the processor is arranged for estimating a flow through the air filter from data representative of a pressure difference (D2) over the fan (F), and a motor current (I) to the motor (M), estimating a filter resistance of the air filter from data representative of the flow through the air filter, and a pressure difference (D1) over the air filter, and estimating pollution of the air filter from data representative of the filter resistance of the air filter.

4. A device as claimed in claim 3, wherein the processor is arranged for estimating the pollution of the air filter from comparing the filter resistance of the air filter with a threshold value (PR).

* * * * *